(12) United States Patent
Hazen

(10) Patent No.: US 8,628,935 B2
(45) Date of Patent: Jan. 14, 2014

(54) PON1 AS A MARKER FOR HEART FAILURE

(75) Inventor: Stanley L. Hazen, Pepper Pike, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 13/390,965

(22) PCT Filed: Aug. 19, 2010

(86) PCT No.: PCT/US2010/046037
§ 371 (c)(1),
(2), (4) Date: Apr. 30, 2012

(87) PCT Pub. No.: WO2011/022563
PCT Pub. Date: Feb. 24, 2011

(65) Prior Publication Data
US 2012/0219979 A1    Aug. 30, 2012

Related U.S. Application Data

(60) Provisional application No. 61/286,681, filed on Dec. 15, 2009, provisional application No. 61/235,242, filed on Aug. 19, 2009.

(51) Int. Cl.
*C12Q 1/44* (2006.01)

(52) U.S. Cl.
USPC .......................................................... 435/19

(58) Field of Classification Search
USPC .......................................................... 435/19
See application file for complete search history.

(56) References Cited

U.S. PATENT DOCUMENTS

2008/0261250 A1* 10/2008 Heinecke et al. ............ 435/7.92
2009/0208992 A1*  8/2009 Hazen et al. .................. 435/19

OTHER PUBLICATIONS

Gur et al., Cornonary Artery Disease, 18(2), 89-95, 2007.*
Linke, Axel, et al., "Antioxidative Effects of Exercise Training in Patients With Chronic Heart Failure: Increase in Radical Scavenger Enzyme Activity in Skeletal Muscle" Circulation published by Journal of American Heart Association, Circulation 2005;111: pp. 1763-1770 (2005).
Hofer, Sabine E., et al., "Association Between PON 1 polymorphisms, PON activity and diabetes complications", Journal of Diabetes and Its Complications, 20 (2006) pp. 322-328.
Keskin, M., et al. "Baseline and salt-stimulated paraoxonase and arylesterase activities in patients with chronic liver disease: relation to disease severity", Internal Medicine Journal 39 (2009) pp. 243-248.
McMurray, J., et al. "Evidence of oxidative stress in chronic heart failure in humans", European Heart Journal (1993) 14, pp. 1493-1498 (Glasgow, Scotland).
Dieterich, Sabine, et al., "Gene Expression of Antioxidative Enzymes in the Human Heart: Increased Expression of Catalase in the End-Stage Failing Heart" Circulation published by Journal of American Heart Association, Circulation 2000; 101; pp. 33-39.
Cracowski, J.L et al., Increased Formation of F2-isoprostanes in patients with severe heart failure, Heart Journal, Heart 2000; 84; pp. 439-440; Scientific Letters.
Diaz-Velez, Carlos R., et al., "Increased malondialdehyde in peripheral blood of patients with congestive heart failure", American Heart Journal, vol. 131, No. 1, pp. 146-152, Jan. 1996.
Sam, Flora, et al., "Increased Reactive Oxygen Species Production and Functional Alterations in Antioxidant Enzymes in Human Failing Myocardium", Journal of Cardiac Failure, Laboratory Investigation, vol. 11, No. 6 (2005) pp. 473-480.
Dirican, M., et al., "Oxidative status and prevalent cardiovascular disease in patients with chronic renal failure treated by hemodialysis", Clinical Nephrology, vol. 68, No. 3/2007, pp. 144-150.
Hare, Joshua A., et al., "Oxidative Stress and Apoptosis in Heart Failure Progression" Circulation Research, published by Journal of American Heart Association, Circulation Res. 2001; 89 (3) pp. 198-200.
Rosenblat, Mira, et al., "Paraoxonases role in the prevention of cardiovascular diseases", International Union of Biochemistry and Molecular Biology, Inc., BioFactors, vol. 35, No. 1, Jan./Feb. 2009, pp. 98-104.
Bhattacharya, Tamali, et al., "Relationship of Paraoxonase 1 (PON1) Gene Polymorphisms and Functional Activity with Systemic Oxidative Stress and Cardiovasular Risk", JAMA. Mar. 19, 2008; 299(11): pp. 1265-1276.
Ungvari, Zoltan, et al., "Role of Oxidative-Nitrosative Stress and Downstream Pathways in Various Forms of Cardiomyopathy and Heart Failure", J Curr Vasc Pharmacol. Jul. 2005; 3(3): pp. 221-229.
Hoening, Michel R., "The Cardiac Microvasculature in Hypertension, Cardiac Hypertrophy and Diastolic Heart Failure", Current Vascular Pharmacology, 2008, vol. 6, No. 4; pp. 292-300.
Gaidukov M.M., Leonid, et al., "The development of human sera tests for HDL-bound serum PON1 and its lipolactonase activity", Israel, Journal of Lipid Resarch, vol. 48 (2007), pp. 1637-1646.
La Du, Bert, "Invited Editorial: The Human Serum Paraoxonase/Arylesterase Polymorphism", Am. J. Hum. Genet. 43: pp. 227-229, (1988).
James, Richard, et al., "The importance of High-Density lipoproteins for paraoxonase-1 secretion, stability, and activity", Free Radical Biology & Medicine, vol. 37, No. 12, pp. 1986-1994 (2004).
Den Uil, Corstian A., et al., "The Microcirculation in Health and Critical Disease", Progress in Cardiovascular Diseases, vol. 51, No. 2 (Sep./Oct.) 2008: pp. 161-170.
Camps, Jordi, et al., "The paraoxonases: role in human diseases and methodological difficulties in measurement", Critical Reviews in Clinical Laboratory Science, 2009, 46(2): pp. 83-106.

(Continued)

*Primary Examiner* — Maryam Monshipouri
(74) *Attorney, Agent, or Firm* — Calfee Halter & Griswold LLP

(57) ABSTRACT

Provided herein are methods for assessing the risk a test subject with heart failure has of experiencing a major adverse cardiac event, requiring revascularization, requiring a heart transplant, requiring unscheduled hospitalization for heart failure, progression of heart failure status, or any combination thereof. Also provided herein are methods for assessing the risk a test subject has of developing heart failure. The present methods comprise determining the levels of paraoxonase 1 activity in the serum, non-chelated plasma, or both in the test subject and comparing the level of PON1 activity in the test subject's sample with a control or baseline value based on levels of PON1 activity in serum, non-chelated plasma, or both samples from a population of control subjects. Also provided herein are kits useful in assessing such risks.

11 Claims, 3 Drawing Sheets

(56) References Cited

OTHER PUBLICATIONS

Hokamanki, Jun., et al., "Urinary Biopyrrins Levels are Elevated in Relation to Severe Heart Failure", Journal of the American College of Cardiology, vol. 43, No. 10 (2004); pp. 1880-1885.

George, Jacob., et al., "Usefulness of anti-oxidized LDL antibody determination for assessment of clinical control in patients with heart failure", The European Journal of Heart Failure, 8 (2006) pp. 48-62.

Shih, Diana M. et al., "Mice Lacking serum paraoxonase are susceptible to organophosphate toxicity and atherosclerosis", Nature; vol. 394, Jul. 16, 2008; pp. 284-287.

Knapp, et al., Clinical Epidemiology and Biostatistics, Harwal Publishing Company, Malvern, PA, copyright 1992, cover page and Table of Contents, 8 pgs.

Mackness Bharti, et al., "Low paraoxanase activity predicts coronary events in the Caerphilly Study", Circulation Jun. 10, 2003, vol. 107, No. 22, pp. 2775-2779.

Kim et al., "Decreased paraoxanase-1 activity is a risk factor for ischemic stroke in Koreans", Biochem. and Biophys. Res. Comm., Academic Press Inc., Orlando FL, vol. 364, No. 1, Oct. 22, 2007, pp. 157-162.

\* cited by examiner

PON1 AS A MARKER FOR HEART FAILURE

CROSS-REFERENCE TO RELATED APPLICATIONS

This application is a 371 of PCT/US10/046037, Aug. 19, 2010, which claims the benefit of U.S. Provisional Application No. 61/235,242, filed Aug. 19, 2009, and U.S. Provisional Application No. 61/286,681, filed Dec. 15, 2009, both of which are incorporated herein by reference in their entirety.

STATEMENT REGARDING FEDERALLY SPONSORED RESEARCH OR DEVELOPMENT

This work was supported by U.S. National Institutes of Health grants P01 HL076491-055328, P01 HL087018-020001, and P01 HL077107-050004. The U.S. government has certain rights in this invention.

BACKGROUND

The present disclosure relates to methods which can be used to determine whether a test subject with heart failure, more particularly a human subject, is at a low risk or high risk of experiencing a major adverse cardiovascular event. It also relates to methods which can be used to determine whether a test subject without heart failure is at a low or high risk of developing heart failure. Also disclosed herein are kits useful for determining suck risks.

Heart failure (HF) is generally defined as inability of the heart to supply sufficient blood flow to meet the body's needs. Common causes of heart failure include myocardial infarction (heart attacks) and other forms of ischemic heart disease, hypertension, valvular heart disease, and cardiomyopathy. Heart failure can cause a number of symptoms including shortness of breath, coughing, chronic venous congestion, ankle swelling, and exercise intolerance. Heart failure is often undiagnosed due to a lack of a universally agreed definition and challenges in definitive diagnosis. Treatment commonly consists of lifestyle measures (such as decreased salt intake) and medications, and sometimes devices or even surgery.

Heart failure is a common, costly, disabling, and potentially deadly condition. In developing countries, around 2% of adults suffer from heart failure, but in those over the age of 65, this increases to 6-10%. Mostly due to costs of hospitalization it is associated with a high health expenditure; costs have been estimated to amount to 2% of the total budget of the National Health Service in the United Kingdom, and more than $35 billion in the United States. Heart failure is associated with significantly reduced physical and mental health, resulting in a markedly decreased quality of life. With the exception of heart failure caused by reversible conditions, the condition usually worsens with time. Although some patients survive many years, progressive disease is associated with an overall annual mortality rate of 10%. Thus, there is a need for methods of determining the risk for experiencing a major adverse cardiac event in a broader spectrum of individuals.

SUMMARY

The present disclosure provides new methods for assessing the risk of experiencing a major adverse cardiac event (MACE) in a test subject with heart failure. The methods comprise determining the level of paraoxonase 1 (PON1) activity in a serum or non-chelated plasma sample from the test subject with heart failure and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of experiencing a MACE.

The present disclosure provides new methods for assessing the risk of developing heart failure in a test subject. In some embodiments the test subject is apparently healthy and does not have heart failure. The methods comprise determining the level of paraoxonase 1 (PON1) activity in a serum or non-chelated plasma sample from the test subject and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of developing heart failure.

As used herein the term "major adverse cardiac event" includes, but is not limited to, non-fatal cerebrovascular accident, non-fatal myocardial infarction, death, or a combination thereof. In some embodiments, heart failure includes, but is not limited to, systolic heart failure, diastolic heart failure, left ventricular dysfunction, or combinations thereof. In some embodiments, the left ventricular dysfunction is characterized by having a lower than normal left ventricular ejection fraction (LVEF). In some embodiments, the LVEF is less than 40%. In some embodiments, non-fatal cerebrovascular accident includes, but is not limited to, stroke, transient ischemic attacks, or both.

In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

Also disclosed herein are methods of determining if the test subject is at near term risk of experiencing a major adverse cardiac event. As used herein, the term "near term" means within three years. Thus, subjects who are at near term risk may be at risk of experiencing a major adverse cardiac event within the following day, 3 months, 6 months, or one year after being tested. In some embodiments the methods are useful for determining if the test subject is at long term risk of experiencing a major adverse cardiac event. As used herein, the term "long term" means within ten years. Thus, subjects who are at long term risk may be at risk of experiencing a major adverse cardiac event within the following five years, seven years, 10 years, or longer after being tested. The present methods are especially useful for identifying those individuals who are at high risk and thus, in need of highly aggressive therapies as well as those individuals who require no therapies targeted at preventing such events.

Also disclosed herein are methods for assessing the risk of the test subject with heart failure requiring revascularization.

The methods comprise determining the level of paraoxonase 1 (PON1) activity in a serum or non-chelated plasma sample from the test subject and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of requiring revascularization.

In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

Also disclosed herein are methods of determining if the test subject is at near term risk of requiring revascularization. As used herein, the term "near term" means within three years. Thus, subjects who are at near term risk may be at risk of requiring revascularization within the following day, 3 months, 6 months, or one year after being tested. In some embodiments the methods are useful for determining if the test subject is at long term risk of requiring revascularization. As used herein, the term "long term" means within ten years. Thus, subjects who are at long term risk may be at risk of requiring revascularization within the following five years, seven years, 10 years, or longer after being tested. The present methods are especially useful for identifying those individuals who are at high risk and thus, in need of highly aggressive therapies as well as those individuals who require no therapies targeted at preventing such events.

Also disclosed herein are methods for assessing the risk of the test subject with heart failure requiring a heart transplant. The methods comprise determining the level of paraoxonase 1 (PON1) activity in a serum or non-chelated plasma sample from the test subject and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of requiring a heart transplant.

In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

Also disclosed herein are methods of determining if the test subject is at near term risk of requiring a heart transplant. As used herein, the term "near term" means within three years. Thus, subjects who are at near term risk may be at risk of requiring a heart transplant within the following day, 3 months, 6 months, or one year after being tested. In some embodiments the methods are useful for determining if the test subject is at long term risk of requiring a heart transplant. As used herein, the term "long term" means within ten years. Thus, subjects who are at long term risk may be at risk of requiring a heart transplant within the following five years, seven years, 10 years, or longer after being tested. The present methods are especially useful for identifying those individuals who are at high risk and thus, in need of highly aggressive therapies as well as those individuals who require no therapies targeted at preventing such events.

Also disclosed herein are methods for assessing the risk of the test subject with heart failure requiring unscheduled hospitalization for heart failure. The methods comprise determining the level of paraoxonase 1 (PON1) activity in a serum or non-chelated plasma sample from the test subject and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of requiring unscheduled hospitalization for heart failure.

In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

Also disclosed herein are methods of determining if the test subject is at near term risk of requiring unscheduled hospitalization for heart failure. As used herein, the term "near term" means within three years. Thus, subjects who are at near term risk may be at risk of requiring unscheduled hospitalization for heart failure within the following day, 3 months, 6 months, or one year after being tested. In some embodiments the methods are useful for determining if the test subject is at long term risk of requiring unscheduled hospitalization for heart failure. As used herein, the term "long term" means within ten years. Thus, subjects who are at long term risk may be at risk of requiring unscheduled hospitalization for heart failure within the following five years, seven years, 10 years, or longer after being tested. The present methods are especially useful for identifying those individuals who are at high risk and thus, in need of highly aggressive therapies as well as those individuals who require no therapies targeted at preventing such events.

Also disclosed herein are methods for assessing the risk of progression of heart failure in the test subject. The methods comprise determining the level of paraoxonase 1 (PON1) activity in a serum or non-chelated plasma sample from the test subject and comparing the level of PON1 activity in the test subject's serum or non-chelated plasma sample with a control or baseline value. The control or baseline value is based on levels of PON1 activity in serum or non-chelated plasma samples from a population of control subjects. A test subject whose level of PON1 activity is less than the control or baseline value is at risk of progression of heart failure.

In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

Also disclosed herein are methods of determining if the test subject is at near term risk of progression of heart failure. As used herein, the term "near term" means within three years. Thus, subjects who are at near term risk may be at risk of progression of heart failure within the following day, 3 months, 6 months, or one year after being tested. In some embodiments the methods are useful for determining if the test subject is at long term risk of progression of heart failure. As used herein, the term "long term" means within ten years. Thus, subjects who are at long term risk may be at risk of progression of heart failure within the following five years, seven years, 10 years, or longer after being tested. The present methods are especially useful for identifying those individuals who are at high risk and thus, in need of highly aggressive therapies as well as those individuals who require no therapies targeted at preventing such events.

Also disclosed herein are kits useful in assessing whether a subject is at risk of at least one of the following: experiencing a MACE; requiring revascularization; requiring a heart transplant; requiring unscheduled hospitalization for heart failure; and progression of heart failure status. The kit may comprise one or more reagents for determining the level of PON1 activity in a subject. In some embodiments, PON1 activity is determined by measuring arylesterase, paraoxonase, lipolactonase, lactonase, or combinations of these activities. These activities can be determined using known methods, including, but not limited to, spectrophotometry. In some embodiments, the spectrophotometry can be chosen from the group consisting of visible, ultraviolet, and fluorescence based spectrophotometry. In some embodiments the kit may further comprise information for assessing the subject's risk of at least one of the following: experiencing a MACE; requiring revascularization; requiring a heart transplant; requiring unscheduled hospitalization for heart failure; and progression of heart failure status.

In some embodiments of the methods, the test subject has no evidence of cardiovascular disease (CVD) or heart failure. As used herein, "evidence of cardiovascular disease" means that the test subject, individual, or patient has no history of CVD and/or less than 50% stenosis of all major coronary vessels. In some embodiments, the control subjects are apparently healthy control subjects. In some embodiments, the apparently healthy control subjects are without any known CVD.

DETAILED DESCRIPTION

Figure 1:
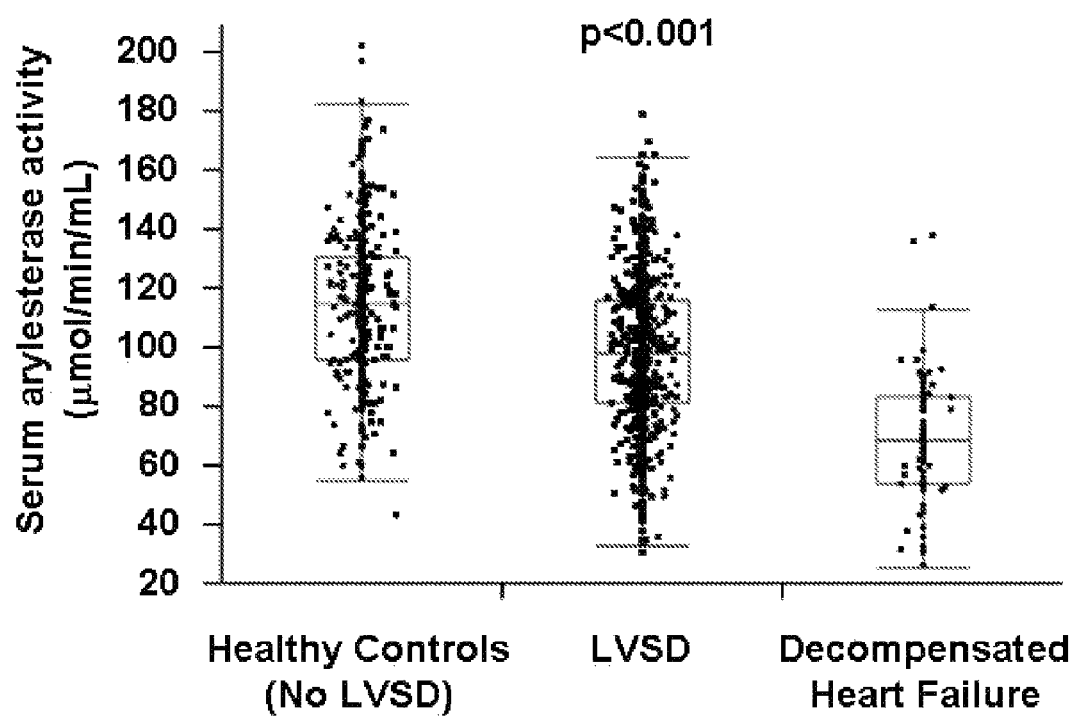
FIG. 1 shows a comparison of serum arylesterase activity between healthy controls (n=300), patients with stable systolic heart failure (n=760), and hospitalized patients with advanced decompensated heart failure (n=75).

The present disclosures will now be described by reference to more detailed embodiments, with occasional reference to the accompanying drawings. These disclosures may, however, be embodied in different forms and should not be construed as limited to the embodiments set forth herein. Rather these embodiments are provided so that this disclosure will be thorough and complete, and will convey the scope of the disclosures to those skilled in the art.

Unless otherwise defined, all technical and scientific terms used herein have the same meaning as commonly understood by one of ordinary skill in the art to which these disclosures belong. The terminology used in the description herein is for describing particular embodiments only and is not intended to be limiting of the disclosures. As used in the description and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, concentrations, and so forth as used in the specification and claims are to be understood as being modified in all instances by the term "about," unless the context indicates otherwise. Accordingly, unless otherwise indicated, the numerical properties set forth in the following specification and claims are approximations that may vary depending on the desired properties sought to be obtained in embodiments of the present disclosures. Notwithstanding that the numerical ranges and parameters setting forth the broad scope of the disclosures are approximations, the numerical values set forth in the specific examples are reported as precisely as possible. Any numerical values, however, inherently contain certain errors necessarily resulting from error found in their respective measurements.

All publications, patent applications, patents, and other references mentioned herein are incorporated by reference in their entirety.

Provided herein are methods of assessing the risk of experiencing a major adverse cardiac event in a subject with heart failure. The methods comprise determining the levels of PON1 activity in a serum, non-chelated plasma, or both types of sample from the subject and are based on the discovery that subjects who have decreased systemic levels of PON1 activity relative to a control or representative value are at greater risk of experiencing a major adverse cardiac that subjects whose systemic levels of PON1 activity are higher relative to a control or representative value.

PON1 enzymatic activity in the subject's serum, non-chelated plasma, or both types of sample can be determined using a number of different substrates. Thus, in one embodiment PON1 enzymatic activity can be determined by measuring arylesterase activity (as described below) in the sample obtained from the test subject. In another embodiment PON1 enzymatic activity can be determined by measuring paraoxonase activity (as described below) in the sample obtained from the test subject. In another embodiment PON1 enzymatic activity can be determined by measuring lipolactonase activity in the sample obtained from the test subject. Methods for measuring such activity are described in Gaidukov L, Tawfik DS. "The development of human sera tests for HDL-bound serum PON1 and its lipolactonase activity" J Lipid Res. 2007 Jul; 48(7):1637-46. In another embodiment PON1 enzymatic activity can be determined by measuring lactonase activity in the sample obtained from the test subject. Methods of measuring lactonase activity are known in the art. The level of PON1 activity in the sample can be determined by measuring the PON1 enzymatic activity in the sample and normalizing this value to obtain the PON1 activity or mass per milliliter of serum, per milliliter of plasma, or per weight.

Preparation of Bodily Sample.

Suitable sources for the bodily samples include but are not limited to whole blood samples, samples of blood fractions, including but not limited to serum and non-chelated plasma. The sample source may be fresh blood or stored blood (e.g., in a blood bank) or blood fractions. The sample source may be a blood sample expressly obtained for the assays disclosed herein or a blood sample obtained for another purpose which can be sub-sampled for the assays disclosed herein.

In one embodiment, the biological sample source is whole blood. Whole blood may be obtained from the subject using standard clinical procedures. In another embodiment, the biological sample source is plasma. Plasma may be obtained from whole blood samples by centrifugation of anti-coagulated blood containing anti-coagulants such as heparin. However, it is preferred that such samples do not contain a metal ion chelator such as EDTA since these types of compounds can inhibit PON1 enzymatic activity. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions, employing one of a variety of buffers, such as phosphate, Tris, or the like, at physiological pH can be used.

Control/Representative Value.

The level of PON1 activity in the bodily sample obtained from the test subject is compared to a control value. The control value is based upon the levels of PON1 activity in comparable samples obtained from the general population or from a select population of human subjects. For example the control value may be derived from serum and/or non-chelated plasma samples obtained from apparently healthy individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. In certain embodiments, the control value may be derived from subjects who have not experienced a major adverse cardiac event within a predetermined period of time, e.g. one to three years, after providing the control sample. In another example, the control value can be derived from an apparently healthy nonsmoker population. "Nonsmoker," as used herein, means an individual who, at the time of the evaluation, is not a smoker. This includes individuals who have never smoked as well as individuals who in the past have smoked but have not smoked in the previous 12 months. An apparently healthy, nonsmoker population may have a different normal range of PON1 enzymatic activity than will a smoking population. Accordingly, the control values selected may take into account the category into which the test subject falls. Appropriate categories can be selected with no more than routine experimentation by those of ordinary skill in the art.

In certain embodiments, the control value can be a baseline value derived by measuring systemic PON1 levels in the subject himself at an earlier time. Thus, the present method can be used to monitor over time the subject's risk of experiencing a major adverse cardiac event.

The control value can take a variety of forms. The control value can be a single cut-off value, such as a median or mean. The control value can be established based upon comparative groups such as where the risk in one defined group is double the risk in another defined group. The control can be a range, for example, where the general population is divided equally (or unequally) into groups, such as a low risk group, a medium risk group and a high-risk group, or into tertiles or quadrants, the lowest tertile or quadrant being individuals with substantially altered risk compared to individuals in the highest tertile or quadrant. In the case of paraoxonase enzymatic activity, which is inversely correlated with cardiac risks, subjects in the lowest tertile or quartile of paraoxonase enzymatic activity have the highest risk, and subjects in the highest tertile or quartile of paraoxonase enzymatic activity have the lowest risk.

Control values of PON1 enzymatic activity, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed.

The levels of PON1 enzymatic activity in the individual's bodily sample may be compared to a single control value or to a range of control values. If the level of PON1 enzymatic activity in the test subject's bodily sample is lower than the control value or range of control values, the test subject is at greater risk of experiencing a major cardiac event than individuals with levels comparable to or above the control value or control range of values. The extent of the difference between the test subject's risk predictor levels and control value is also useful for characterizing the extent of the risk and thereby, determining which individuals would most greatly benefit from certain aggressive therapies. In those cases, wherein the control value ranges are divided into a plurality of groups, such as the control value ranges for individuals at high risk, average risk, and low risk, the comparison involves determining into which group the test subject's level of the relevant risk predictor falls.

The present methods are useful for determining if and when certain therapies, including therapeutic agents, which are targeted at preventing major adverse cardiac events should and should not be prescribed for a patient. For example, individuals with values of PON1 activity below a certain cutoff value, or that are in the lower tertile or quartile of a "normal range," could be identified as those in need of more aggressive intervention.

The present methods are also useful for identifying individuals at increased risk of experiencing a major cardiovascular event who might otherwise not have been identified by existing screening protocols/methods.

In another aspect, the present disclosure provides methods of determining the risk for requiring revascularization as defined by angioplasty, stenting, and coronary artery bypass grafting (CABG) in a subject. In some embodiments the subject has no evidence of coronary artery disease. The method comprises determining the levels of PON1 enzymatic activity in the subject's serum, non-chelated plasma, or both. A subject whose levels of PON1 activity are low relative to a control value based on levels of PON1 activity in samples from the general population or a select population is a greater risk of requiring revascularization than a subject whose systemic levels of PON 1 enzymatic activity are high relative to the control value.

Also disclosed herein are methods of determining the risk for requiring a heart transplant in a subject. In some embodiments the subject has no evidence of coronary artery disease. The method comprises determining the levels of PON1 enzymatic activity in the subject's serum, non-chelated plasma, or both. A subject whose levels of PON1 activity are low relative to a control value based on levels of PON 1 activity in samples from the general population or a select population is a greater risk of requiring a heart transplant than a subject whose systemic levels of PON1 enzymatic activity are high relative to the control value.

Also disclosed herein are methods of determining the risk unscheduled hospitalization for heart failure in a subject. In some embodiments the subject has no evidence of coronary artery disease. The method comprises determining the levels of PON1 enzymatic activity in the subject's serum, non-chelated plasma, or both. A subject whose levels of PON1 activity are low relative to a control value based on levels of PON1 activity in samples from the general population or a select population is a greater risk of requiring unscheduled hospitalization for heart failure than a subject whose systemic levels of PON 1 enzymatic activity are high relative to the control value.

Also disclosed herein are methods of determining the risk progression of heart failure status in a subject. In some embodiments the subject has no evidence of coronary artery disease. The method comprises determining the levels of PON1 enzymatic activity in the subject's serum, non-chelated plasma, or both. A subject whose levels of PON1 activity are low relative to a control value based on levels of PON1 activity in samples from the general population or a select population is a greater risk of progression of heart failure status than a subject whose systemic levels of PON1 enzymatic activity are high relative to the control value.

In another aspect, the present disclosure provides methods of determining whether a subject who has experienced a major adverse cardiac event is at risk of experiencing a recurrent major cardiovascular event, e.g., reinfarction. The method comprises determining the levels of PON1 activity in the subject's sample. A subject whose levels of PON1 activity are low relative to a control value based on levels of PON1 activity in samples from the general population or a select population is a greater risk of experiencing recurrent or subsequent major adverse cardiac event than a subject whose systemic levels of PON1 enzymatic activity are high relative to the control value.

EXAMPLES

The following examples are for illustration only and are not intended to limit the scope of the disclosures.

Diminished serum arylesterase activity, catalyzed by the HDL-associated paraoxonase-1 (PON1), is associated with heightened systemic oxidative stress and atherosclerosis risk. The role of serum arylesterase activity in systolic heart failure, particularly in relation with established cardiac biomarkers, is unknown.

Serum arylesterase activity was measured in 760 subjects with impaired left ventricular systolic function (left ventricular ejection fraction [LVEF] <50%), and the subjects were prospectively followed for major adverse cardiac events (MACE, including for example death, non-fatal myocardial infarction, and stroke) for 3 years. In the study cohort (mean age 64±11 years, 74% male, median LVEF 35%, median creatinine clearance [CrCl] 87 mg/dL), mean serum arylesterase activity was lower than healthy controls but higher than those with advanced decompensated heart failure (mean 98 ±25 µmol/min/mL). Within the cohort, there was modest inverse correlation between serum arylesterase activity and B-type natriuretic peptide (BNP, r=-0.23, p<0.01), and weak correlations were observed between serum arylesterase activity and LVEF (Spearman's r=0.12, p<0.01) and high-sensitivity C-reactive protein (hsCRP, r=-0.13, p<0.01). Lower serum arylesterase activity was a strong predictor of poorer outcomes (Quartile 4 versus Quartile 1, Hazard ratio 3.27, 95% confidence intervals 1.66-6.44, p<0.001). After adjusting for log(BNP), log(hsCRP), Framingham risk factors, and CrCl, the lowest three quartiles of arylesterase still maintain a 2.6-fold increased risk in MACE at 3 years (Q4 vs. lower 3 quartiles, Hazard ratio 2.59 [1.34, 4.99], p=0.004).

In patients with systolic heart failure, decreased PON1 activity, an HDL associated protein with a strong link to systemic indices of oxidant stress, predicts higher long-term adverse cardiac event rates independent of established clinical and biochemical risk factors.

Introduction

Oxidative stress plays an important role in the pathogenesis and progression of heart failure[1,2]. Different degrees of oxidative stress are operative in the syndrome of heart failure and cardiac dysfunction, ranging from direct damage to cellular proteins and membranes (leading to apoptosis and necrosis), to alterations in cardiac energetics or extracellular matrix remodeling. Measures of stable oxidative byproducts, including oxidized low-density lipoproteins (LDL)[7], malondialdehyde[8], isoprostaines[9], and urinary bioptyrins[10], are increased in the setting of heart failure. However, reactive oxidant species and their byproducts are often transient, compartmentalized, and difficult to quantify in vivo, which has led to the search for indirect markers of oxidative stress.

Increased oxidative stress results from an imbalance between reactive oxygen, nitrogen, and halogenating species and endogenous antioxidant defense mechanisms to scavenge free radicals and their byproducts[4,5], such as superoxide dismutase, catalase, glutathione peroxidase[3]. Therefore, an imbalance between oxidative and anti-oxidative mechanisms may lead to deleterious consequences[6]. Paraoxonase-1 (PON1) is a high density lipoprotein (HDL)-associated glycoprotein believed to play a key role facilitating systemic anti-oxidant activities of HDL, including the remodeling of oxidized phospholipids[11,12]. PON1 is produced by the liver, and catalyzes calcium-dependent esterase and lactonase activities critical to its lipid remodeling and systemic anti-oxidant functions. Numerous studies have shown that PON1 serves as a primary contributor to systemic (serum) arylesterase activity (hydrolase activity on carboxylic ester bonds such as phenyl acetate)[13]. Systemic measures of PON1 activity, such as serum arylesterase activity, have been shown to have strong correlations with multiple systemic measures of oxidant stress, including multiple distinct fatty acid oxidation products quantified by liquid chromatography with on-line stable isotope dilution tandem mass spectrometryl[3]. Thus, both human clinical investigations[13], and studies employing PON1 knockout mice (Shih DM, Gu L, Xia YR, Navab M, Li W F, Hama S, Castellani L W, Furlong C E, Costa L G, Fogelman A M, Lusis A J. Nature. 1998 Jul 16;394(6690):284-7. Rozenberg O, Rosenblat M, Coleman R, Shih D M, Aviram M. Free Radic Biol Med. 2003 Mar 15;34(6):774-84.) are consistent with PON1 serving a major anti-oxidant function in vivo. Herein, the potential role of serum PON1 activity was examined, as monitored by arylesterase activity measurements, as a predictor of adverse disease progression among patients with systolic heart failure.

Methods

Study population. The Cleveland Clinic GeneBank study is a large (n>10,000), prospective cohort study from 2001-2006 that established a well-characterized clinical repository with clinical and longitudinal outcomes data comprised from consenting subjects undergoing elective diagnostic cardiac catheterization procedure not in the setting of acute coronary syndrome. All GeneBank participants gave written informed consent approved by the Cleveland Clinic Institutional Review Board. Clinical outcomes were prospectively ascertained over the ensuing 3 years for all subjects following enrollment. Major adverse cardiovascular event (MACE) was defined as all-cause mortality, non-fatal myocardial infarction, or non-fatal cerebrovascular accident following enrollment.

This analysis included 760 consecutive subjects with stable systolic heart failure (left ventricular ejection fraction [LVEF] <50% as determined by echocardiography, radionuclide or contrast ventriculography) enrolled in GeneBank with serum samples available for analysis. The Framingham Risk Score was calculated for each subject as standard cardiovascular risk factors. An estimate of creatinine clearance (CrCl) was calculated using the Cockcroft-Gault equation. High sensitivity C-reactive protein (hsCRP), B-type natriuretic peptide (BNP), creatinine, and fasting blood glucose and lipid profiles were measured on the Abbott Architect platform (Abbott Laboratories, Abbott Park Ill.).

Serum arylesterase activity assay. Serum arylesterase activity was measured by UV spectrophotometry in a 96-well plate format (Spectramax 384 Plus, Molecular Devices, Sunnyvale, Calif.) using phenyl acetate (Sigma-Aldrich, St Louis, Miss.) as substrate. Briefly, initial hydrolysis rates were determined at 270 nm in 50-fold diluted serum (final) in reactions mixtures composed of 3.4 mM phenylacetate, 9 mM Tris hydrochloride, pH 8, and 0.9 mM calcium chloride at 24° C. An extinction coefficient (at 270 nm) of 1310 M-1·cm-1 was used for calculating units of arylesterase activity, which are expressed as the amount of phenyl acetate hydrolyzed in $\mu$M/min/mL of serum. The intra-assay and inter-assay coefficients of variance for performance of arylesterase were 1.2% and 3.9%, respectively, on 20 replicates performed on 10 different days.

To examine the range of serum arylesterase activity using this assay, a cross-sectional comparison was performed between the cohort of stable systolic heart failure with a separate set of apparently healthy control subjects without known cardiac diseases from a health screen (n=300), as well as a group of consecutive patients with advanced decompensated heart failure admitted to the heart failure intensive care unit for hemodynamically-guided therapy including intravenous diuretic therapy (n=73), all with written informed consent approved by the Cleveland Clinic Institutional Review Board.

Statistical analyses. The Student's t-test or Wilcoxon-Rank sum test for continuous variables and chi-square test for categorical variables were used to examine the difference between the groups. Receiver Operator Characteristic (ROC) curve analyses were performed to determine the optimal cut-off at 121 $\mu$M/min/mL, with risk of event estimated using 5-fold cross-validation by a Cox model and logistic regression model. Adjustments were made for individual traditional cardiac risk factor, Framingham Risk Score, log-transformed hsCRP, log-transformed BNP, and CrCl to predict incident 3-year MACE risks. Kaplan-Meier analysis with Cox proportional hazards regression was used for time-to-event analysis to determine Hazard ratio (HR) and 95% confidence intervals (95% CI) for MACE. All analyses were performed using SAS version 8.2 (Cary, N.C.) and R 2.8.0 (Vienna, Austria). P values <0.05 were considered statistically significant.

Results

Study population. Table 1 describes the baseline characteristics of the subjects, which is a relatively well-compensated patient cohort with median systolic ejection fraction of 35%, normal mean creatinine clearance of 100±41 ml/min/1.73 m$^2$, 63% ACE inhibitor use, and 40% treated with standing diuretic therapy. Serum arylesterase levels were normally distributed, with a mean of 98±25 $\mu$M/min/mL, which was lower than that in apparently healthy control population (mean 115±26 $\mu$M/min/mL, p<0.01, FIG. 1), but higher than that of hospitalized patients with advanced systolic heart failure (mean 69±22 $\mu$M/min/mL, p<0.01). In general, male subjects tended to have lower serum arylesterase activity levels than female subjects.

TABLE 1

Baseline Subject Characteristics.

| Variable | Value |
| --- | --- |
| Age (years) | 64 ± 11 |
| Male (%) | 74 |
| Diabetes mellitus (%) | 40 |
| Hypertension (%) | 72 |
| Ischemic etiology (%) | 68 |
| LDL cholesterol (mg/dL) | 101 (81, 120) |
| HDL cholesterol (mg/dL) | 32 (26, 38) |
| Triglycerides (mg/dL) | 119 (87, 167) |
| B-type natriuretic peptide (mg/dL) | 193 (86, 481) |
| hsCRP (mg/L) | 2.7 (1.2, 6.9) |
| LV Ejection Fraction (%-units) | 35 (30, 45) |
| Creatinine clearance (ml/min/1.73 m$^2$) | 100 ± 41 |
| Aspirin (%) | 73 |
| Statins (%) | 62 |
| Diuretics (%) | 40 |
| ACE inhibitors (%) | 63 |
| Beta-blockers (%) | 67 |

Values expressed in mean±standard deviation or median (interquartile range). Abbreviations: cTnI=LDL=low-density lipoprotein; HDL=high-density lipoprotein; hsCRP=high-sensitivity C-reactive protein; ATP III=Adult Treatment Panel III guidelines.

Serum arylesterase levels and cardiac biomarkers. There was modest inverse correlation between serum arylesterase and plasma B-type natriuretic peptide levels (BNP, r=-0.23, p<0.01). In contrast, weaker correlations were observed between arylesterase levels and LVEF (Spearman's r=0.12, p<0.01) and high-sensitivity C-reactive protein (hsCRP, r=-0.13, p<0.01). In logistic regression models, male gender, BNP, and hsCRP were independent predictors of elevated serum arylesterase levels (Table 2).

TABLE 2

Logistic regression model for determinants of serum arylesterase levels.

|  | Estimate | Standard Error | z-value | p-value |
| --- | --- | --- | --- | --- |
| Age | −0.001 | 0.009 | −0.128 | 0.898 |
| Gender | −0.634 | 0.189 | −3.358 | <0.001 |
| Creatinine clearance | 0.002 | 0.003 | 0.950 | 0.342 |
| BNP | −0.332 | 0.076 | −4.380 | <0.001 |
| LV ejection fraction | 0.005 | 0.009 | 0.559 | 0.576 |
| Diabetes mellitus | −0.104 | 0.160 | −0.649 | 0.517 |
| Hypertension | 0.209 | 0.174 | 1.206 | 0.228 |
| hsCRP | −0.009 | 0.004 | −2046 | 0.04 |

Abbreviations:
BNP = B-type natriuretic peptide;
LV = left ventricle;
hsCRP = high-sensitivity C-reactive protein.

Figure 2:
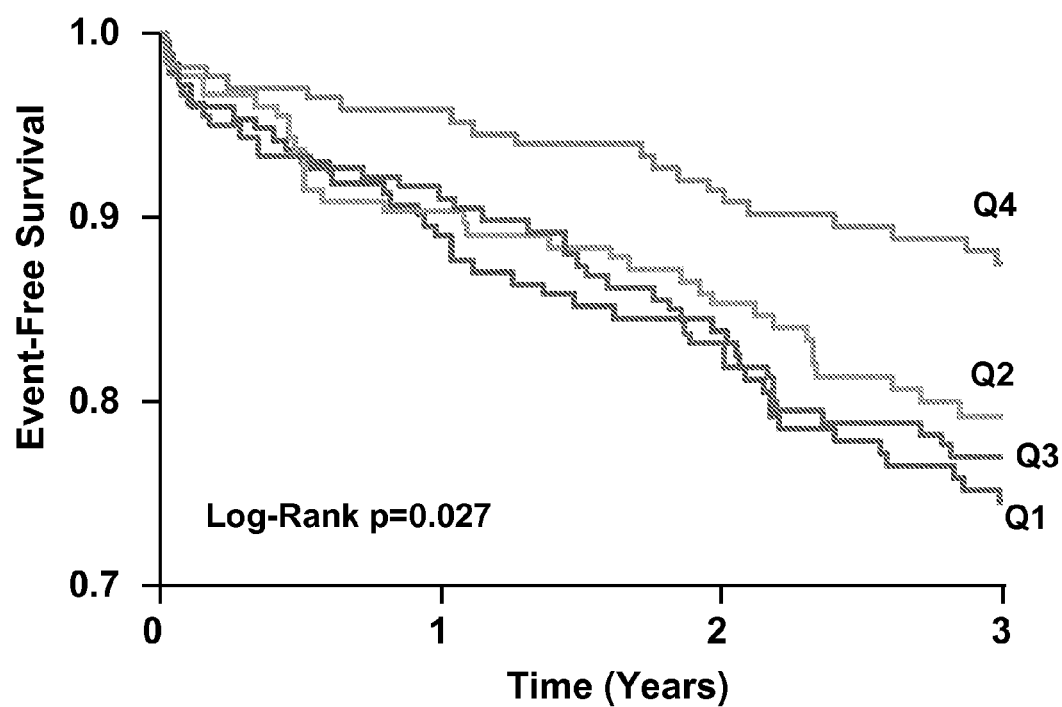
FIG. 2 shows Kaplan-Meier analysis for long-term major adverse cardiac events stratified by serum arylesterase quartiles (Log-rank, p=0.027); quartile ranges as followed: Q1: <82 µM/min/mL; Q2: 82-97 µM/min/mL; Q3: 98-116; Q4: >116.
Figure 3:
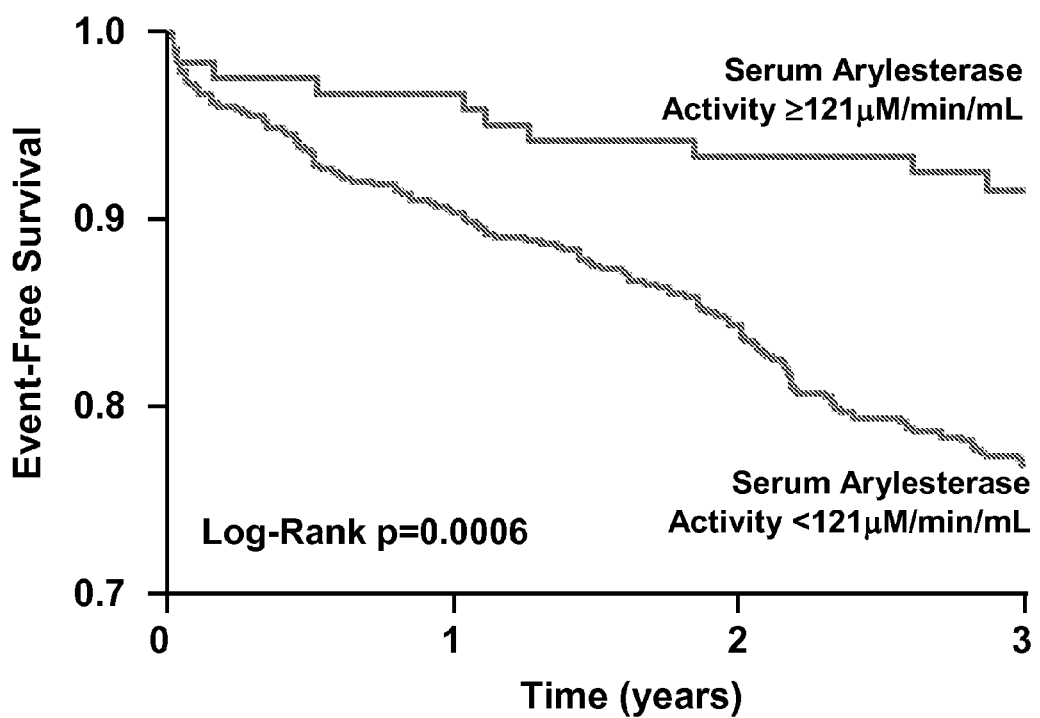
FIG. 3 shows Kaplan-Meier analysis for long-term major adverse cardiac events stratified by optimal cut-off of 121 µM/min/mL (Log-rank, p=0.006).

Serum arylesterase levels and major adverse cardiac outcomes. A total of 134 events (non-fatal MI, stroke or death) were recorded within the 3-year period of follow-up. Lower serum arylesterase activity was associated with poorer long-term outcomes when stratified by quartiles (Hazard ratios [95% confidence interval] for Q4 vs. Q3: 1.99 [1.16-3.41], p=0.01; Q4 vs. Q2: 1.87 [1.08-3.24], p=0.02; Q4 vs. Q1: 2.18 [1.28, 3.73], p<0.001). When Kaplan-Meier analysis was performed (stratified according to quartiles) there was clear distinction between the highest quartile (cut-off at 116 μM/min/mL) and the lower three quartiles (HR 1.98 [1.23, 3.18], p=0.005, FIG. 2). Kaplan-Meier analysis demonstrated heightened risk associated with the development of MACE at 3 years when stratified at the ROC-determined optimal cut-off level of 121 μM/min/mL (HR 2.94 [1.54, 5.62], p=0.001, FIG. 3). After adjusting for log(BNP), log(hsCRP), Framingham risk factors, and CrCl, lower serum arylesterase levels still maintains a robust 2.6-fold increased risk in the development of MACE at 3 years (HR 2.59 [1.34, 4.99], p=0.004, Table 3; FIG. 3).

TABLE 3

|  | Hazard Ratio 95% confidence (interval) | p value |
| --- | --- | --- |
| Univariate Model |  |  |
| Arylesterase activity <121 μM/min/mL | 2.94 (1.54, 5.62) | 0.001 |
| Multivariate Model |  |  |
| Arylesterase activity <121 μM/min/mL | 2.59 (1.34, 4.99) | 0.004 |
| Log (BNP) | 1.25 (1.08, 1.45) | 0.003 |
| Log (hsCRP) | 1.18 (1.04, 1.33) | 0.008 |
| Framingham Risk Score | 1.05 (0.99, 1.11) | 0.09 |
| Creatinine Clearance | 1.00 (0.99, 1.00) | 0.23 |

Discussion

The major findings of this study is the demonstration of a robust association between low PON1 activity measures, as monitored by serum arylesterase activity levels, and poor long-term prognosis in patients with impaired LV systolic function. The prognostic value of serum arylesterase activity levels within the cohort was both independent of, and stronger than, standard cardiac prognostic indices of disease severity within heart failure patients, such as BNP. There were also notable differences in serum arylesterase activity between the study population of stable patients with impaired LV systolic function and those admitted with advanced decompensated systolic heart failure. These observations are in parallel with reports of prognostic value of other oxidative stress markers in patients with heart failure, but performed in a large scale using a high-throughput platform. What is unique in the findings is the potential identification and quantification of an important anti-oxidative pathway that is broadly affected in the setting of cardiac dysfunction, thereby providing opportunities to modulate or enhance such pathways in treating systolic heart failure.

PON1 activity measurement, such as with arylesterase activity, is readily detectable in human serum, and low arylesterase activity has been associated with increased systemic measures of oxidative stress, heightened cardiovascular disease risk[13], and increased disease severity in other end-organ dysfunction[14,15]. Instead of indirectly measuring byproducts of oxidative stress, quantifying serum arylesterase activity levels facilitates a direct measurement of the anti-oxidative process that has been previously described in protecting organophosphate toxicity[6] and reducing atherosclerotic cardiovascular risk in humans[13,17] and animal models (Shih D M, Gu L, Xia Y R, Navab M, Li W F, Hama S, Castellani L W, Furlong C E, Costa L G, Fogelman A M, Lusis A J. Nature. 1998 Jul 16;394(6690):284-7). The ability of arylesterase levels to predict long-term outcomes independently of standard prognostic markers such as BNP in this population is intriguing, especially when the strength of risk prediction for serum arylesterase activity appeared robust. The strong prognostic value of serum arylesterase activity is not linear, as the lowest three quartiles of subjects had poorer outcomes compared to the highest quartiles. This finding may imply that a clinical meaningful "cut-off" should be employed for defining a high-risk cohort, which represented a broad systolic heart failure population. In contrast, those with relatively preserved (high) serum arylesterase activity may also be reassured that they are in a relatively lower risk category for long-term adverse cardiac events.

The precise pathophysiologic mechanism of PON1 activity in human heart failure has not been previously examined. The expression and variability of systemic arylesterase activity over the natural history of heart failure is largely unknown, although it is conceivable that reduced serum arylesterase activity can adversely contribute to disease progression in a number of ways. The best described mechanism is the association between PON1 activity and protection of lipoprotein oxidation that antagonizes progression of atherosclerotic coronary artery disease, a major cause of heart failure in Western societies. Another potential protective mechanism for arylesterase activity may include the possibility for limiting microvascular dysfunction as a result of endothelial dysfunction[18,19]. Indeed, lower serum PON1/arylesterase activity has been reported in patients with cardiac syndrome X[20], and genetic polymorphisms favoring preserved PON1/arylesterase are protective of microvascular diseases in patients with diabetes mellitus[21].

REFERENCES

1. Hare J M. Oxidative stress and apoptosis in heart failure progression. *Circ Res.* 2001;89(3):198-200.
2. McMurray J, Chopra M, Abdullah I, Smith W E, Dargie H J. Evidence of oxidative stress in chronic heart failure in humans. *Eur Heart J.* 1993;14(11):1493-1498.
3. Linke A, Adams V, Schulze P C, Erbs S, Gielen S, Fiehn E, Mobius-Winkler S, Schubert A, Schuler G, Hambrecht R. Antioxidative effects of exercise training in patients with chronic heart failure: increase in radical scavenger enzyme activity in skeletal muscle. *Circulation.* 2005;111(14): 1763-1770.
4. Dieterich S, Bieligk U, Beulich K, Hasenfuss G, Prestle J. Gene expression of antioxidative enzymes in the human heart: increased expression of catalase in the end-stage failing heart. *Circulation.* 2000;101(1):33-39.
5. Sam F, Kerstetter D L, Pimental D R, Mulukutla S, Tabaee A, Bristow M R, Colucci W S, Sawyer D B. Increased reactive oxygen species production and functional alterations in antioxidant enzymes in human failing myocardium. *J Card Fail.* 2005;11(6):473-480.
6. Ungvari Z, Gupte S A, Recchia F A, Batkai S, Pacher P. Role of oxidative-nitrosative stress and downstream pathways in various forms of cardiomyopathy and heart failure. *Curr Vasc Pharmacol.* 2005;3(3):221-229.
7. George J, Wexler D, Roth A, Barak T, Sheps D, Keren G. Usefulness of anti-oxidized LDL antibody determination for assessment of clinical control in patients with heart failure. *Eur J Heart Fail.* 2006;8(1):58-62.
8. Diaz-Velez C R, Garcia-Castineiras S, Mendoza-Ramos E, Hernandez-Lopez E. Increased malondialdehyde in peripheral blood of patients with congestive heart failure. *Am Heart J.* 1996;131(1):146-152.
9. Cracowski J L, Tremel F, Marpeau C, Baguet J P, Stanke-Labesque F, Mallion J M, Bessard G. Increased formation of F(2)-isoprostanes in patients with severe heart failure. *Heart.* 2000;84(4):439-440.
10. Hokamaki J, Kawano H, Yoshimura M, Soejima H, Miyamoto S, Kajiwara I, Kojima S, Sakamoto T, Sugiyama S, Hirai N, Shimomura H, Nagayoshi Y, Tsujita K, Shioji I, Sasaki S, Ogawa H. Urinary biopyrrins levels are elevated in relation to severity of heart failure. *J Am Coll Cardiol.* 2004;43(10):1880-1885.
11. James RW, Deakin SP. The importance of high-density lipoproteins for paraoxonase-1 secretion, stability, and activity. *Free Radic Biol Med.* 2004;37(12):1986-1994.
12. Rosenblat M, Aviram M. Paraoxonases role in the prevention of cardiovascular diseases. *Biofactors.* 2009;35 (1):98-104.
13. Bhattacharyya T, Nicholls S J, Topol E J, Zhang R, Yang X, Schmitt D, Fu X, Shao M, Brennan D M, Ellis S G, Brennan M L, Allayee H, Lusis A J, Hazen S L. Relationship of paraoxonase 1 (PON1) gene polymorphisms and functional activity with systemic oxidative stress and cardiovascular risk. *JAMA.* 2008;299(11):1265-1276.
14. Dirican M, Sarandol E, Serdar Z, Ocak N, Dilek K. Oxidative status and prevalent cardiovascular disease in patients with chronic renal failure treated by hemodialysis. *Clin Nephrol.* 2007;68(3):144-150.
15. Keskin M, Dolar E, Dirican M, Kiyici M, Yilmaz Y, Gurel S, Nak S G, Erdinc S, Gulten M. Baseline and salt-stimulated paraoxonase and arylesterase activities in patients with chronic liver disease: relation to disease severity. *Intern Med J.* 2009;39(4):243-248.
16. Camps J, Marsillach J, Joven J. The paraoxonases: role in human diseases and methodological difficulties in measurement. *Crit Rev Clin Lab Sci.* 2009;46(2):83-106.
17. La Du BN. The human serum paraoxonase/arylesterase polymorphism. *Am J Hum Genet.* 1988;43(3):227-229.
18. den Uil C A, Klijn E, Lagrand W K, Brugts J J, Ince C, Spronk P E, Simoons M L. The microcirculation in health and critical disease. *Prog Cardiovasc Dis.* 2008;51(2):161-170.
19. Hoenig M R, Bianchi C, Rosenzweig A, Sellke F W. The cardiac microvasculature in hypertension, cardiac hypertrophy and diastolic heart failure. *Curr Vasc Pharmacol.* 2008;6(4):292-300.
20. Gur M, Yildiz A, Demirbag R, Yilmaz R, Aslan M, Ozdogru I, Erel O. Paraoxonase and arylesterase activities in patients with cardiac syndrome X, and their relationship with oxidative stress markers. *Coron Artery Dis.* 2007;18 (2):89-95.
21. Hofer S E, Bennetts B, Chan A K, Holloway B, Karschimkus C, Jenkins A J, Silink M, Donaghue K C. Association between PON 1 polymorphisms, PON activity and diabetes complications. *J Diabetes Complications.* 2006; 20(5):322-328.

The invention claimed is:

1. A method for assessing a risk of experiencing a major adverse cardiac event (MACE) in a test subject with heart failure comprising:
    determining a level of paraoxonase 1 (PON1) activity in a serum or non-chelated plasma sample from the test subject; and
    comparing the level of PON1 activity in the test subject's serum or non-chelated plasma sample with a control or baseline value based on levels of PON 1 activity in serum or non-chelated plasma samples from a population of control subjects, wherein a test subject whose level of PON 1 activity is less than the control or baseline value is at risk of experiencing a MACE.

2. The method of claim 1, wherein the MACE is selected from the group consisting of: nonfatal cerebrovascular accident; non-fatal myocardial infarction (MI); and death.

3. The method of claim 2, wherein the non-fatal cerebrovascular accident is selected from the group consisting of: stroke and transient ischemic attacks.

4. The method of claim 1, wherein the test subject's heart failure is selected from the group consisting of: systolic heart failure, diastolic heart failure, and left ventricular dysfunction.

5. The method of claim 1, wherein the PON1 activity is determined by measuring arylesterase, paraoxonase, lipolactonase, or lactonase activity in the subject's serum or non-chelated plasma sample.

6. The method of claim 5, wherein the arylesterase, paraoxonase, lipolactonase, or lactonase activity is determined by spectrophotometry.

7. The method of claim 1, wherein the control subjects are apparently healthy control subjects.

8. The method of claim 7, wherein the apparently healthy control subjects are without any known cardiac diseases.

9. The method of claim 1, wherein the test subject whose level of PON1 activity is less than the control or baseline value is at risk of experiencing a MACE within 3 years.

10. The method of claim 1, wherein the test subject whose level of PON1 activity is less than the control or baseline value is at risk of experiencing a MACE within 10 years.

11. A method for assessing a risk of developing heart failure in a test subject comprising:
   determining a level of PON1 activity in a serum or non-chelated plasma sample from the test subject; and
   comparing the level of PON1 activity in the test subject's serum or non-chelated plasma sample with a control or baseline value based on levels of PON 1 activity in serum or non-chelated plasma samples from a population of control subjects, wherein a test subject whose level of PON 1 activity is less than the control or baseline value is at risk of developing heart failure.

* * * * *

UNITED STATES PATENT AND TRADEMARK OFFICE
CERTIFICATE OF CORRECTION

PATENT NO. : 8,628,935 B2
APPLICATION NO. : 13/390965
DATED : January 14, 2014
INVENTOR(S) : Stanley L. Hazen Page 1 of 1

It is certified that error appears in the above-identified patent and that said Letters Patent is hereby corrected as shown below:

In the Specification

In Column 1, Lines 15-18 should read:
This invention was made with government support under HL076491, HL087018 and HL077107 awarded by the National Institutes of Health. The government has certain rights in the invention.

Signed and Sealed this
Twentieth Day of October, 2020

Andrei Iancu
*Director of the United States Patent and Trademark Office*